(12) United States Patent
Hersh

(10) Patent No.: US 6,303,651 B1
(45) Date of Patent: *Oct. 16, 2001

(54) SYNERGISTIC ANTIOXIDANT VETERINARY COMPOSITIONS

(75) Inventor: Theodore Hersh, Atlanta, GA (US)

(73) Assignee: Thione International, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/404,050

(22) Filed: Sep. 23, 1999

(51) Int. Cl.$^7$ ............... A61K 31/197; A61K 31/28; A61K 31/315; A61K 33/24; A61K 33/30

(52) U.S. Cl. ............ 514/492; 514/345; 514/458; 514/474; 514/494; 514/554; 514/556; 514/562; 514/829; 514/830; 514/859; 514/861; 514/863; 514/875; 514/886; 514/887; 514/937; 514/944; 424/94.4; 424/641; 424/642; 424/702

(58) Field of Search ............... 514/562, 492, 514/859, 861, 863, 875, 886, 887, 345, 458, 474, 494, 554, 556, 829, 830, 937, 944; 424/94.4, 641, 642, 702

(56) References Cited

U.S. PATENT DOCUMENTS

| | | | |
|---|---|---|---|
| 5,667,791 | * 9/1997 | Hersh et al. | 424/401 |
| 5,827,886 | * 10/1998 | Hersh | 514/562 |
| 5,939,394 | * 8/1999 | Fleming et al. | 514/23 |
| 6,011,067 | * 1/2000 | Hersh | 514/562 |
| 6,231,889 | * 5/2001 | Richardson et al. | 424/464 |
| 6,242,010 | * 6/2001 | Hersh | 424/702 |

FOREIGN PATENT DOCUMENTS

3542309 * 6/1987 (DE) .

OTHER PUBLICATIONS

Derwent Abstract, Accession No. 1987–157985, abstracting DE 3,542,309, 1987.*

Chemical Abstracts 129:288074e, 1998.*

Chemical Abstracts 128:201850n, 1998.*

* cited by examiner

Primary Examiner—John Pak
(74) Attorney, Agent, or Firm—Malcolm B. Wittenberg

(57) ABSTRACT

A composition and method of treating cutaneous infection and resulting inflammation in animals known as hot spots and mange, respectively, as well as related veterinarian dermatological conditions. The composition includes L-glutathione and a source of selenium which act synergistically and which are included in a suitable topical carrier for topical application.

13 Claims, No Drawings

SYNERGISTIC ANTIOXIDANT VETERINARY COMPOSITIONS

TECHNICAL FIELD OF THE INVENTION

The present invention deals with combinations of several synergistic antioxidants including enzymatic co-factors as adjunct to therapies of various mammals, particularly canine, feline and equine inflammatory conditions, including but not limited to thermal and chemical burns, various types of dermatitis, eczema infections and flea and mite induced cutaneous lesions, commonly known as "hot spots" and mange, respectively. These topical compositions are aimed at scavenging and neutralizing reactive oxygen species and other free radicals generated in the cutaneous inflammatory reactions being responsible for the animal's clinical symptoms and cutaneous lesions. These novel therapeutic compounds may be combined with other state of the art topical active ingredients such as zinc salts, anti-inflammatories (salicylates, non-steriodal anti-inflammatory drugs) corticosteroids, anti-microbials for the treatment of secondary bacterial or fungal infections and healing anti-oxidants such as zinc pyrithione and vitamins C and E.

BACKGROUND OF THE INVENTION

Canine eczema, clinically known as dermatitis rubric madidans, is one of the most difficult dermatologic problems to treat in veterinary medicine. Its pathogenesis is still rudimentary and multiple therapies are available to treat symptoms, while antibiotics quell secondary infections. Older literature refers to this entity as a moist and desquamating eczema or as infectious dermatitis, as the etiology was theorized to be Staphylococcus aureus as the putative pathogen. This Staph was cultured from early lesions, thus the term "infectious dermatitis." Staph toxins or an "allergic id" reaction were postulated as etiologic. Contact dermatitis might also play a role in this condition.

Clinically, this eczema presents an acute discomfort, is persistent, and tends to recur. It is more frequent in the mature dog rather than in puppies. The lesions are of sudden onset and spread rapidly. The affected areas are very sensitive and extremely pruritic. The animal may have premonitory symptoms which include restlessness, anorexia, vomiting, and itching. Animals tend to persist in scratching, biting and rubbing the affected sensitive, moist lesions which become yellow to light red in color. Their efforts to obtain relief of the pruritus by scratching not only extends the depth and surface area of the dermatitis, but the excriations cause infection which extend to areas adjoining the original eczematoid site. Fever and lymph node enlargement may be noted. The course of this eczematoid reaction is variable, depending on the extent of the lesion, degree of destruction of the cutaneous tissues, severity of secondary infection and the animal's response to therapy.

Infections of the skin, so-called integumentary infections in dogs and cats, are most frequently caused by bacterial or fungal infectious agents. The cutaneous microbial flora comprises both resident and transient bacterial inhabitants. The former tends to be consistent in types and colonies within an anatomic area and is usually harmless. Resident bacteria have the usual characteristic of inhibiting the growth of skin pathogenic bacteria.

Other factors maintaining the resident communal microflora include skin pH and moisture, sebum production and the healthy status of the outer skin layer, the stratum corneum. Under adverse conditions to the aforementioned cutaneous factors which may disrupt the normal bacterial barriers, both the resident (usual) bacteria and the transient bacterial invaders may cause the cutaneous infectious lesion called pyoderma. In dogs, Staphylococcus aureus is a normal skin inhabitant but may increase its colony numbers in traumatized, inflamed or seborrheic animal skin conditions. Staph may reside in the hair, and these bacteria are apt to be the source of secondary infection causing pyoderma, with the classic symptoms of the animals' "hot spots".

While Staph aereus is the major pathogen isolated from dogs' pyoderma, both local and systemic immune responses are probably involved in the pathogenesis of pyoderma. While specific anti-microbials are mandatory for the eradication of the pathogen causing pyoderma, both symptomatic and anti-inflammatory therapy to these cutaneous lesions is mandatory. The synergistic antioxidant compositions of the present invention are designed to scavenge and neutralize the reactive oxygen and other free radical species, which are present in the inflammatory reactions of these cutaneous primary and secondary infections and inflammatory reactions. Pustules, papules and furuncles require specific anti-microbial therapies, plus symptomatic therapies, including the reduction of inflammatory free radical reactions by the present antioxidant synergistic components to enhance the animal's cutaneous endogenous antioxidant defenses and promote the healing reparative processes.

Secondary skin lesions, the pyodermas, are characterized by excoriations, and ulcerations and crusting. Excoriations are self-inflicted lesious leading to ulcers, which are commonly referred to as "hot spots". These "hot spots" are not truly pyoderma but are very bothersome and symptomatic to these domestic animals. Erosions and ulcers are secondary lesions, which result from the putative inflammatory process and/or from the victim's self-mutilation symptomatic response to the itching and pain. These are followed by classic signs of infection, namely, exudation, swelling and exaggerated redness and pus. The eroded and ulcerated tissues must be treated to alleviate the symptoms, and to reduce the inflammation. These remedies include compositions such as topicals containing the synergistic antioxidant complex of the present invention. Scarring needs to be prevented. Finally, if untreated, these secondary lesions, called "crusts" developing from dried exudates and keratin, must be carefully removed by the clinician in an effort to promote healing and avoid scarring of these tissues.

Infestation by fleas is common in domestic animals, particularly in dogs and cats, but fleas are not uncommon in other hairy mammals. Fleas are small, wingless bloodsucking external parasites, mainly of the species Ctenocephalides, genus *felis* for cats and genus *canis* for dogs. The adult flea spends most of its life on the body of the host. Eggs laid on the host or in the ground hatch into larvae feeding on organic matter. The larvae then spins a loose cocoon that within six days, under optimum conditions, becomes an adult then the insect emerges from the cocoon, and seeks the appropriate host, like these domestic animals, in order to feed on them and thereby continue their insect life cycle.

Adult fleas feed only on blood of the host animal. In this "nutrition and survival cycle"0 of the fleas, they cause their hosts intense itching (pruritus) with consequent irritation to the host, which evokes a response to scratch and bite the affected irritated skin in an effort to control the pruritic and inflammatory site of the hypersensitive host skin.

The fleas cause the irritating symptoms due to their constant biting of the host's skin and from the flea's salivary secretion of toxic agents and allergens. Particularly in hypersensitive domestic host animals, fleabites produce intense pruritus and the animal then scratches and bites the putative skin surfaces. These mammals become restless from the cutaneous irritation and they continue biting and scratching in an attempt to relieve the irritating symptoms. By this mechanism, the host produces an acute, discrete dermatitis, which has also commonly been called a "hot spot". Also, the biting and scratching may yield a chronic, nonspecific dermatitis, including ulceration and moist desquamation from the flea infested sites. The "hot spots" in the dog are usually subauricular, interscapular or adjacent to their rumps or thighs. In contrast, the chronic, non-specific flea induced dermatitis is more apt to be restricted to the lower back and to the perineum. Secondary infection from skin bacteria is common in both syndromes and may follow from the self-inflicted trauma of the host to a cycle of constant irritation, pruritus, ulceration and desquamation of the affected skin areas.

Diagnosis of these flea induced "hot spots" depends on careful examination of the "hot spots" and adjacent tissues for fleas or debris of fleas in the hair follicles. Fleas may also be found in large numbers in the head, rump or tail of the affected domestic animal.

Treatment is bi-modal and requires both symptomatic and specific therapy of the inflamed, ulcerated, and desquamated cutaneous lesions as well as eradication of the pathogen, the offending fleas. Insecticides may remove fleas from the host (pyrethrum or rotenone powders). Control of flea breeding places is environmentally imperative.

Treatment of the host is directed at controlling symptoms of itching and discomfort, to alleviate the animal's biting and scratching. The second line of therapy of "hot spots" is directed to reduce the inflammation and the toxic free radical species generated in this inflammatory reaction. One of the roles of this invention is in providing antioxidants which by scavenging and neutralizing free radicals in "hot spots," inflammation is reduced. By applying the present group of antioxidants based on L-glutathione and its synergistic antioxidant compositions, one is able to combat the skin's free radicals and the fleas' other toxic secretions and thereby heal "hot spots".

The antioxidant compositions of this invention may include as optional ingredients antimicrobials including antibiotics to help combat the secondary bacterial infections of these cutaneous, flea created "hot spots". These compositions may also contain the specific flea killing insecticides, as well as compounds known to provide anti-pruritic and soothing cutaneous effects to the animals' "hot spots". In summary, the compositions of this invention are based on antioxidants to ameliorate the inflammatory reaction and can optionally include as topical preparations compounds to provide both symptomatic and antimicrobial therapeutic effects such as bacitracin, neomycin, and/or polysporin. Oral or parenteral agents with anti-inflammatories can also be included such as cortisone, prednisolone, and aspirin or non-steroidal anti-inflammaries, plus optionally, tranquilizers and phenobarbital derivatives. Vital adjuncts in the management of "hot spots" include cleansing of the dermatitic, ulcerated areas with standard soaps and anti-microbial lotions, ideally with hexachlorophene. The mainstay to reduce inflammation and promote healing of "hot spots" is the use of the present antioxidant complex with eradication of the fleas.

Domestic animals not infrequently become infected with mites, which may cause pronounced itching with swelling and irritation of their skin. The itching may be severe necessitating the animal to scratch causing the skin to ulcerate. Symptoms are worse in warm weather. Secondary skin infections are serious complications. The intense scratching also spreads the mite, aggravating this condition which is known as sarcoptic mange. To establish the diagnosis, the causative mite needs to be identified and then eradicated by specific pesticide therapy. The animal's mite induced dermatitis and ulcerations require symptomatic treatment; the synergistic antioxidant compositions of this invention are used to reduce the redness and swelling of the inflammatory reaction while the zinc moieties help heal these sarcoptic mange lesions.

Another related condition which may also be treated with these antioxidant complexes to reduce redness, swelling and itching is called demodectic or red mange. This is caused by a small and elongated mite called Demodex folliculorum, which lives deep in the hair follicles, thereby becoming a more permanent invading parasite. Red mange in the dog usually starts in the head, around the eyes and then spreads producing a severe dermatitis with inflammation, thus the name red mange. Treatment again is directed at eliminating the mite, such as with Ivermectin, and along with the symptomatic therapy as the antioxidant compositions of this invention to reduce the inflammation, redness and itching. Oral Ivermectin has also been used for therapy of generalized demodicosis or scabies with good results.

SUMMARY OF THE INVENTION

The present invention is directed to a composition and method of treating cutaneous infection and resulting inflammation in animals including eczema, hot spots and related dermatological conditions. The invention includes treating hot spots which result from flea and mite bites as well as from various other skin-related conditions. The composition comprises the combination of L-glutathione and selenium that act synergistically.

DETAILED DESCRIPTION OF THE INVENTION

The present invention, as noted above, is based upon an L-glutathione containing antioxidant complex. The complex is thought to work as follows.

The major functions of reduced glutathione (GSH) in protection against lipid peroxidation are related to three types of reactions, all inter-related and synergistic combining non-enzymic scavengers and enzymic and dietary provided antioxidants.

1. GSH with selenium co-factor glutathione peroxidases eliminate toxic peroxides.

2. GSH reduces oxidized forms of vitamin C which, in turn, maintains vitamin E in its reduced form promoting its metabolic functions. Thus, GSH supports the free radical reductions and free radical chain-terminating functions of the two nutrient antioxidants, vitamin C and E.

3. GSH functions through gluathione S-transferases to detoxify reactive aldehydes created during the process of lipid peroxidation in the tissues of canine's with hot spots and other dermatoses.

Some cells have sodium dependent up-take systems for GSH, allowing cells to use both exogenous GSH and endogenously synthesized GSH, thereby enhancing a cell's ability to survive oxidative stress from free radical species damage. In this fashion, extra-cellular GSH also protects cells' survival. Investigative studies have shown that a cells' viability correlates best with content of GSH in mitochondria. In the absence of GSH, lipid peroxidation is uncontrolled and leads to cell injury and death, thereby aggravating the putaive cutaneous lesions. Conversely, GSH protects cells from the ravages of free radicals, working synergistically with the antioxidant enzymes and the dietary vitamin antioxidants, thus helping in the canine's skin repair processes.

Cysteine, one of the three amino acid constituents of GSH, has the "SH" group and thus, on its own, this thiol also possesses antioxidant properties. Therefore, it has been utilized as such or as a cysteine derivative, like N-acetyl-L-cysteine, for dermatologic, oral and other preparations. It is the treatment of choice in hepatic toxicity by acetaminophen (Tylenol). Hildebrand, in U.S. Pat. No. 5,296,500 (Mar. 22, 1994), which is herein incorporated by reference, discloses the use of N-acetyl-L-cysteine for regulating wrinkling and atrophy of the human skin. Hildebrand also teaches cysteine for use in pharmacologically acceptable salts, including zinc compounds. The reference's list of zinc salts does not include zinc pyrithione nor does this patent deal with therapy canine eczema, hot spots or other dermatoses. Sharpe et al in U.S. Pat. No. 5,637,616 (Jun. 10, 1997), which is herein incorporated by reference, teaches the use of topical preparations with effective amounts of N-acetyl-L-cysteine in human diseases mediated by proteases.

However, none of the art considered above, taken either singly or in combination teach the use of reduced glutathione and a selenium source such as a selenoamino acid and N-acetyl-L-cysteine for treating canine eczema, hot spots and as adjuncts to other inflammatory and infectious reactions.

The dermatologics of this invention, namely, the use of the disclosed glutathione antioxidant synergistic group represents a new adjunct to therapy of hot spots and related disease to combat free radical species created by the inflammatory condition. The synergistic antioxidant complex may be combined with other topical ingredients with known beneficial effects such as anti-inflammatory agents, corticosteriods, or anti-microbials such as zinc pyrithione. In addition, these compositions generally contain moisturizers as is known in the art of these therapeutics to help heal the skin lesions as described.

Without being bound to any particular theory, it is noted that reduced glutathione is employed in protecting cells and aerobic organisms against oxidative stress by itself being oxidized. Thus, L-glutathione must act in combination with other enzyme systems, like glutathione reductase, in order to be reduced so that it may renew its role as a free radical scavenger. GSH functions also coordinately with the enzyme glutathione peroxidase which requires selenium as a co-factor to exert its biologic antioxidant function.

Selenium compounds have been shown to scavenge oxygen-centered radicals in vivo with reduced glutathione through glutathione peroxidase. It is believed that selenium-GSH peroxidase catalyzes toxic hydrogen peroxide in the presence of reduced glutathione (GSSG). In turn, the GSSG is reduced back to GSH to scavenge free radicals anew. GSH reductase may be provided in these preparations through thiol rich yeast extracts or wheat germ extracts.

Further, glutathione and selenium act synergistically in vivo as they are both constituents of the same enzymatic system. GSH serves as a specific donor substrate while selenium, provided from alimentary sources or locally from topically applied preparations of selenoamino acids, selenium yeast extracts or selenoamino acid chelates, provides the prosthetic group of GSH peroxidase. The glutathione and selenium antioxidant functions are intrinsically related since by keeping a peroxidase in action, the GSH and selenium, contribute to the removal of the dismutation product of free oxygen radicals, namely, hydrogen peroxide. In a broad sense, GSH and selenium modulate free radical chains initiated or sustained by hydro peroxides.

Selenium is used in the present invention for its role as an antioxidant as well as for its antimutagenic properties. Selenomethionine decomposes lipid peroxides and inhibits in vivo lipid peroxidation. Other selenoproteins also show a high degree of inhibition of lipid peroxidation in hepatic tissues of various species.

Compositions of reduced glutathione of the present invention comprise from about 0.001% to 15%, preferably from about 0.01% to 10%, more preferably from about 0.1% to 5% by weight.

As further noted from several of the examples which follow, the present invention further contemplates the use of additional optional expedients, such as superoxide dismutase (SOD). SOD is a ubiquitous cellular enzyme whose main function is in protecting cells against oxidative stress. Superoxide dismutases are a family of cytosolic metaloenzymes which specifically remove free oxygen radicals. There are three distinct forms of SOD, namely, CUZN SOD, MN SOD and extracellular SOD (EC-SOD). The differences in the SODs is in their amino acid sequence and the location of the transition metals at the active sites. It is hypothesized that the enzyme SOD, along with glutathione peroxidase and its selenium cofactor are effective preventative and repair antioxidants because they eliminate molecules involved in the initiation of free radical reactions. SOD also protects intracellular reduced glutathione against free radical mediated chain oxidation as the combination of SOD and reduced glutathione prevents redox cycling reactions. It is noted that Kalopissis et al., in U.S. Pat. No. 4,129,644, (Oct. 10, 1975) discloses the use of superoxide dismutase (SOD) for maintaining the keratinic structure of hair. SOD was also taught for protecting the skin from harmful effects of ultraviolet rays while also maintaining the skin's keratinic structure.

Vitamins, as those included in these preparations, are naturally derived from dietary fruits and sources, particularly ascorbates, carotenoids, and tocopherols. Natural and synthetic vitamins may be taken orally as supplements or added to animal feeds or as the topical pharmaceutic preparations of this invention.

Vitamin E, particularly in its alpha-tocopherol moiety, has been employed to inhibit oxidation of oils and fats in foods, cosmetic preparations and drugs. Vitamin E is not only an antioxidant but also has anti-inflammatory properties. In skin, vitamin E levels are present in dermis and epidermis, but are depleted by malnutrition, by infection and by ultraviolet light, thus their importance in providing these to act in vivo as antioxidants. Vitamin E moisturizes, enhances skin smoothness and also participates in skin repair and wound healing, such as occurs in hot spots and other animal dermatoses.

Cell membranes and plasma lipoproteins contain alpha tocopherol, which is a lipid soluble molecule that functions as a chain breaking (reparative) antioxidant. An —OH attached to the hydrophobic structure of tocopherol easily releases its hydrogen atom, so that peroxyl and alkoxyl free radicals generated during lipid peroxidation then may combine with this antioxidant instead of with adjacent fatty acid side chains, thereby terminating this chain reaction process of lipid peroxidation. Experimental evidence shows that the tocopherol radical migrates to the membrane surface. It is then reconverted to alpha tocopherol by its reaction with ascorbic acid (vitamin C). Thus, vitamins E and C are synergistic and minimize the toxic effects on lipid peroxidation in cell membranes and lipoproteins. Moreover, glutathione and selenium also act synergistically with vitamin E, the former, GSH, by regenerating alpha tocopherol from its tocopheroxyl radical form. Also, vitamin C and E, selenium and glutathione, in experimental animals, have been shown to work together as antioxidants in skin healing.

Ascorbic acid, vitamin C, plays a significant role in skin metabolism and in synthesis of collagen as a co-factor in hydroxylation reactions for the formation and function of collagen. High vitamin C levels not only stimulate collagen but also reverse epidermal thinning and offer skin protection against ultraviolet rays. These properties of vitamin C are enhanced by using glucosamine where the polyamine complex protects the ascorbic acid, enhancing the antioxidant and anti-collagenase properties of these products. Vitamin C in protective liposomes or other micro-encapsulated lotion techniques may also be used.

Ascorbates can repair oxidizing radicals directly and are therefore characterized as chain-breaking antioxidants. Vitamin C, a water soluble exogenous small molecule antioxidant, is located in aqueous phases of cells while, as noted, vitamin E is in the lipid portion of membranes. Together they protect lipids and lipid structures against peroxidation. Vitamin C repairs the tocopheroxyl radical and permits that molecule to function again as a tocopherol free radical chain-breaking antioxidant. The ascorbate free radical produced in this reaction with tocopherol can be removed from the tissues by a dismutation reaction. The dehydroascorbate and the ascorbate radical can then be removed by enzyme systems that use NADH or NADPH as sources of reducing molecules. Thereby, ascorbate is recycled to protect against the process of lipid peroxidation by its synergistic function with vitamin E.

Thus, topical preparations of the present invention will, in their preferred form, contain mixtures of vitamins C and E to enhance locally the antioxidant activities of the active ingredients, particularly in their function as chain-breaking antioxidants in lipid peroxidation.

Vitamins C and E not only work together as antioxidants in hydrophilic and hydrophobic areas of cells and cell membranes, but also work synergistically with reduced glutathione and the glutathione cascade, including selenium dependent glutathione peroxidase, and superoxide dismutase. Further beneficial pharmacologic effects are additive by using these in protective and enhancing encapsulating reservoir molecules, such as liposomes, nanospheres, glycospheres and others well known to those in the industry.

In a preferred embodiment, the compositions of the present invention are enhanced by the addition of zinc salts. Zinc may function by its healing properties as on wounds, particularly as zinc oxide, and also to render the present preparations odorless, presumably by removing traces of hydrogen sulfide, which could emanate from sulfur groups used in these preparations. Zinc may also be administered as one of the trace metals prepared in yeast extracts as mineral (zinc) glycopeptides. Compositions preferably comprise from about 0.001% to about 8% of a zinc salt, more preferably from about 0.01% to about 4%, more preferably still from about 0.1% to about 1.25%.

Zinc pyrithione has been used in a number of dermatologic preparations, including shampoos, sprays, creams and lotions. It is available in commercial preparations for management of, seborrhoeic dermatitis, flakes (as in psoriasis) and other human skin maladies. Purportedly, this zinc salt possesses antibacterial and antifungal properties, while with its -SH group, it may also function as an antioxidant like GSH.

The medical literature has several reports of the beneficial use of zinc pyrithione alone in psoriatic patients. For example, U.S. Pat. No. 4,323,558 dated Apr. 5, 1982, teaches pharmaceutical compositions containing triethylenetetramine (Trien) for use in various human inflammatory skin disorders, with inclusion of zinc pyrithione with which Trien forms a clear solution or gel. U.S. Pat. No. 4,938,969 dated Jul. 3, 1990 teaches the use of non-toxic zinc salts in topical applications with ascorbic acid and tyrosine as a method for treatment of human aging skin and photodamaged skin. Other pyrithione salts have been disclosed such as sodium, magnesium, copper and chitosanpyrithione, with purported anti-bacterial and anti-fungal properties. The latter compound is disclosed in U.S. Pat. Nos. 5,015,632, 4,345,080 and 4,379,753, which are herein incorporated by reference, disclosing methods for preparing pyrithione crystals that yield the efdesired pearlescence in hair care compositions.

Corticosterioids and other anti-inflammatories may also be added from the families of salicylates and the non-steroidals such as ibuprofen, indomethacin, and others also known in this pharmacology industry. Antibacterial, fungistatic and fungicidal agents may also be employed in these compositions. Specific anti-microbials may be added to the zinc pyrithione-antioxidant agents when treating the putative micro-organism in canine infectious lesions.

The active ingredients described above can be incorporated in any suitable pharmacologically acceptable carrier which is suitable for topical administration to the animal skin. As such, the pharmacologically acceptable carrier must be of sufficient purity and have sufficiently low toxicity to render it suitable for administration.

Typical compositions for use herein include a wide variety of physical forms. These include, but are not limited to, solutions, lotions, creams, oils, gels, sticks, sprays, ointments, balms, shampoo and pastes. Generally, such carrier systems can be described as being solutions, emulsions, gels, solids and aerosols.

Solvents are generally employed in the preparation of suitable topical compositions. Such solvents can either be aqueous or organic based and, in either case, the solvent must be capable of having dispersed or dissolved therein the above-described active components while not being irritating to the animal being treated. Water is a typical aqueous solvent while suitable organic solvents include propylene glycol, butylene glycol, polyethylene glycol, polypropylene glycol, glycerol, 1,2,4-butanetriol, sorbitol esters, 1,2,6-hexanetriol, ethanol, isopropanol, butanediol and mixtures thereof. Solvents can be included in the overall composition in amounts ranging from 0.1% to 99% and preferably from 2.0% to 75%. It is noted that compositions of the present invention can be produced in the form of an emollient. A wide variety of suitable emollients are known and may be used herein. In this regard, reference is made to U.S. Pat. No. 5,296,500, the disclosure of which is incorporated herein by reference.

Alternatively, the present composition can be formulated as a lotion containing from about 0.01% to 10% of the above-described active ingredients. Further, the product can be formulated from a solution carrier system as a cream. A cream of the present invention would preferably comprise from about 0.1% to 15% and preferably from 1% to 5% of the above described active ingredients. Lotions and creams can be formulated as emulsions as well as solutions.

It is contemplated that as one embodiment, the active ingredients described above be used as a lotion or cream emulsion of the oil-in-water type or as a water-in-oil type, both of which being extremely well known in the field. Multi-phase emulsions such as the water-in-oil type are disclosed in U.S. Pat. No. 4,254,105, the disclosure of which is incorporated herein by reference. The compositions may also be administered as a liquid, as in the different type of sprays available in this industry.

It is further contemplated that the active ingredients of the present invention be formulated from a solution carrier system as an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may comprise from 1% to 99% of an emollient plus to about 0.1% to 99% of a thickening agent. Reference is again made to U.S. Pat. No. 5,296,500 and the citations contained therein for a more complete disclosure of the various ointment, cream and lotion formulations for use herein.

It is important to supply locally both L-glutathione (in its reduced form) and synergistic antioxidants to restore epidermal glutathione levels and enhance the reparative antioxidant chain-breaking reactions. The ideal selenium source is a selenoaminoacid such as selenomethionine or selenocysteine. What follows are a set of exemplary formulations.

| | Ingredients | Percent |
|---|---|---|
| | Example 1 (Cream) | |
| 1. | L-glutathione (reduced) | 0.20 |
| 2. | L-selenomethionine | 0.05 |
| 3. | N-acetyl-L-cysteine | 0.25 |
| 4. | A,C,E Liposome | 2.50 |
| 5. | Superoxide dismutase | 0.25 |
| 6. | Zinc pyrithione | 0.25 |
| | Example 2 (Spray) | |
| 1. | L-glutathione (reduced) | 0.20 |
| 2. | L-selenomethionine | 0.05 |
| 3. | N-acetyl-L-cysteine | 0.25 |
| 4. | A,C,E Liposome | 2.50 |
| 5. | Superoxide dismutase | 0.25 |
| 6. | Zinc pyrithione | 0.25 |
| | Example 3 (Shampoo) | |
| 1. | L-glutathioine (reduced) | 0.20 |
| 2. | L-selenomethionine | 0.025 |
| 3. | N-acetyl-L-cysteine | 0.25 |
| 4. | A,C,E Liposome | 1.00 |
| 5. | Superoxide dismutase | 0.10 |
| 6. | Dex-panthenol | 0.5 |
| 7. | Zinc pyrithione | 0.5 |

I claim:

1. A method for treating cutaneous infection and resulting inflammation in nonhuman animals comprising topically applying to the skin of a nonhuman animal in need of treatment for cutaneous infection and resulting inflammation an effective amount of a composition of L-glutathione and a source of selenium in a topical carrier to treat said cutaneous infection and resulting inflammation.

2. The method of claim 1 wherein said carrier is in the form of a member selected from the group consisting of a lotion, cream, gel, emulsion and spray.

3. The method of claim 1 wherein said selenium is a selenoamino acid.

4. The method of claim 3 wherein said selenoamino acid is a member selected from the group consisting of selenomethionine and selenocysteine.

5. The method of claim 1 further comprising an N-acetyl-L-cysteine.

6. The method of claim 1 wherein said composition further comprises superoxide dismutase.

7. The method of claim 1 wherein said composition further comprises a zinc salt.

8. The method of claim 7 wherein said zinc salt comprises zinc pyrithione.

9. The method of claim 1 wherein said composition further comprises Vitamins C and E.

10. The method of claim 1 wherein said L-glutathione is present in said composition in an amount between approximately 0.001 to 15% by weight based upon the weight of the composition.

11. The method of claim 1 wherein said L-glutathione is present in said composition in an amount between approximately 0.01 to 10% by weight based upon the weight of the composition.

12. The method of claim 1 wherein said L-glutathione is present in said composition in an amount between approximately 0.1 to 5% by weight based upon the weight of the composition.

13. A composition for treating pruritus and inflammation resulting from flea bites and mite bites in animals, said composition comprising L-glutathione, selenium and an insecticide in a suitable topical carrier for topical application wherein said L-glutathione, selenium and insecticide are present in said carrier in an effective amount to so treat said pruritus and inflammation.

* * * * *